США012125001B2

United States Patent
Sugimoto et al.

(10) Patent No.: US 12,125,001 B2
(45) Date of Patent: Oct. 22, 2024

(54) SERVER, CHARGING SYSTEM, AND COMPUTER READABLE RECORDING MEDIUM

(71) Applicant: TOYOTA JIDOSHA KABUSHIKI KAISHA, Toyota (JP)

(72) Inventors: Kazuhiro Sugimoto, Ashigarakami-gun (JP); Kotoru Sato, Susono (JP); Kumiko Katsumata, Susono (JP); Shun Ota, Susono (JP); Takahiro Suzuki, Susono (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 512 days.

(21) Appl. No.: 17/477,988

(22) Filed: Sep. 17, 2021

(65) Prior Publication Data

US 2022/0164775 A1 May 26, 2022

(30) Foreign Application Priority Data

Nov. 26, 2020 (JP) .................. 2020-196101

(51) Int. Cl.
| | |
|---|---|
| *G06Q 10/1093* | (2023.01) |
| *B60L 53/60* | (2019.01) |
| *G16H 10/60* | (2018.01) |
| *G16H 50/30* | (2018.01) |
| *H02J 7/00* | (2006.01) |
| *A61B 5/00* | (2006.01) |
| *G01W 1/10* | (2006.01) |

(Continued)

(52) U.S. Cl.
CPC .......... *G06Q 10/1093* (2013.01); *B60L 53/60* (2019.02); *G16H 10/60* (2018.01); *G16H 50/30* (2018.01); *H02J 7/0013* (2013.01); *H02J 7/0071* (2020.01); *A61B 5/7282* (2013.01); *G01W 1/10* (2013.01); *G16H 40/67* (2018.01); *G16H 50/70* (2018.01)

(58) Field of Classification Search
CPC ........ B60L 53/60; H02J 7/0071; H02J 7/0013
USPC .......................................................... 320/109
See application file for complete search history.

(56) References Cited

U.S. PATENT DOCUMENTS

| | | | |
|---|---|---|---|
| 2008/0007202 A1* | 1/2008 | Pryor ................... | B60L 53/14 320/104 |
| 2009/0115251 A1 | 5/2009 | Nakamura et al. | |
| 2019/0095872 A1* | 3/2019 | Lalwani ............ | G06Q 30/0633 |

(Continued)

FOREIGN PATENT DOCUMENTS

| | | | |
|---|---|---|---|
| CA | 02648972 | * | 6/2009 |
| JP | 2007-143370 A | | 6/2007 |
| JP | 2013-030030 A | | 2/2013 |

OTHER PUBLICATIONS

Relevant Description of CA02648972, 146 pages (Year: 2009).*

*Primary Examiner* — Nathaniel R Pelton
(74) *Attorney, Agent, or Firm* — Finnegan, Henderson, Farabow, Garrett, and Dunner, LLP (57) ABSTRACT

A server includes a processor configured to: acquire schedule information on each of a plurality of users; set a charging priority at a time of charging each of a plurality of moving objects based on the schedule information on each of the plurality of users, each of the plurality of moving objects being preliminarily associated with each of the plurality of users, and including a rechargeable secondary battery; and charge each of the plurality of moving objects based on the charging priority.

14 Claims, 6 Drawing Sheets

(51) Int. Cl.
  *G16H 40/67* (2018.01)
  *G16H 50/70* (2018.01)

(56) References Cited

U.S. PATENT DOCUMENTS

2019/0202304 A1* 7/2019 Moghe .................... B60L 53/38
2020/0262307 A1* 8/2020 Rosene ................... H04L 67/12
2021/0203177 A1* 7/2021 Peng ....................... B60L 53/63
2021/0394634 A1* 12/2021 Lu ........................... B60L 53/65

* cited by examiner

SERVER, CHARGING SYSTEM, AND COMPUTER READABLE RECORDING MEDIUM

The present application claims priority to and incorporates by reference the entire contents of Japanese Patent Application No. 2020-196101 filed in Japan on Nov. 26, 2020.

BACKGROUND

The present disclosure relates to a server, a charging system, and a computer readable recording medium.

There has been known a technique of preferentially supplying commercial power to an electric vehicle having the smallest state of charge (SOC) among SOCs of power storage devices. The SOCs are acquired from a plurality of electric vehicles. The power storage devices include a secondary battery mounted in each of the electric vehicles.

SUMMARY

In the known technique, however, power is supplied in order from a charging device having the smaller SOC regardless of whether or not a moving object such as an electric vehicle is scheduled to be used after being charged. Therefore, charging of a moving object to be used may fail to be completed at the time when the moving object is used, so that a user may not use the moving object.

There is a need for a server, a charging system, and a computer readable recording medium that are able to charge a moving object in consideration of timing when a user uses the moving object.

According to one aspect of the present disclosure, there is provided a server including a processor configured to: acquire schedule information on each of a plurality of users; set a charging priority at a time of charging each of a plurality of moving objects based on the schedule information on each of the plurality of users, each of the plurality of moving objects being preliminarily associated with each of the plurality of users, and including a rechargeable secondary battery; and charge each of the plurality of moving objects based on the charging priority.

DETAILED DESCRIPTION

Hereinafter, a charging system according to an embodiment of the present disclosure will be described with reference to the drawings. Note that the present disclosure is not limited by the following embodiment. Furthermore, in the following description, the same sign is attached to the same part.

Hereinafter, a charging system according to the embodiment will be described with reference to the drawings. Note that the present disclosure is not limited by the following embodiment. Furthermore, in the following description, the same sign is attached to the same part.

Figure 1:
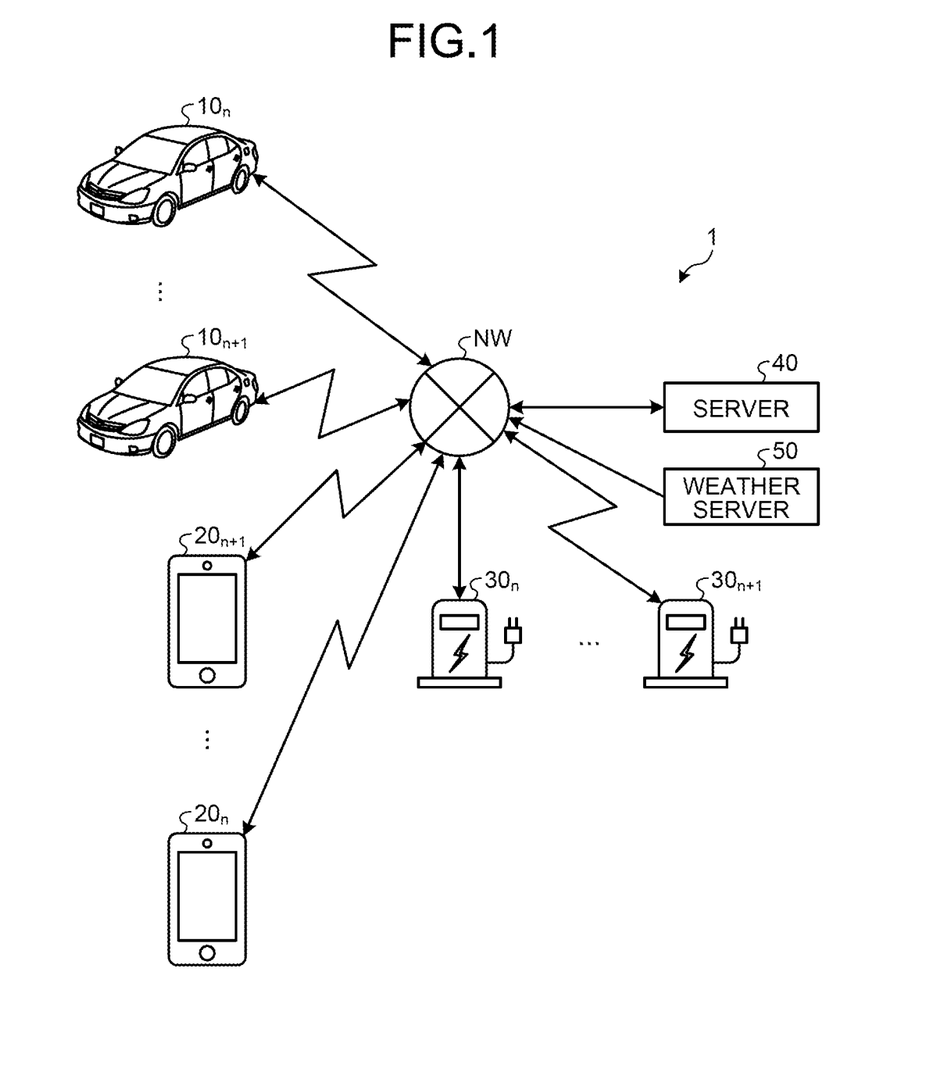
FIG. 1 schematically illustrates the configuration of a charging system according to an embodiment.

FIG. 1 schematically illustrates the configuration of a charging system according to the embodiment. A charging system 1 in FIG. 1 includes moving objects $10_n$ to $10_{n+1}$ (n is integer of 1 or more), communication terminals $20_n$ to $20_{n+1}$, charging devices $30_n$ to $30_{n+1}$, a server 40, and a weather server 50. The weather server 50 stores weather forecasts predicted for each predetermined area. The charging system 1 may communicate with each other over a network NW. The network NW includes, for example, an internet network and a mobile phone network.

Figure 2:
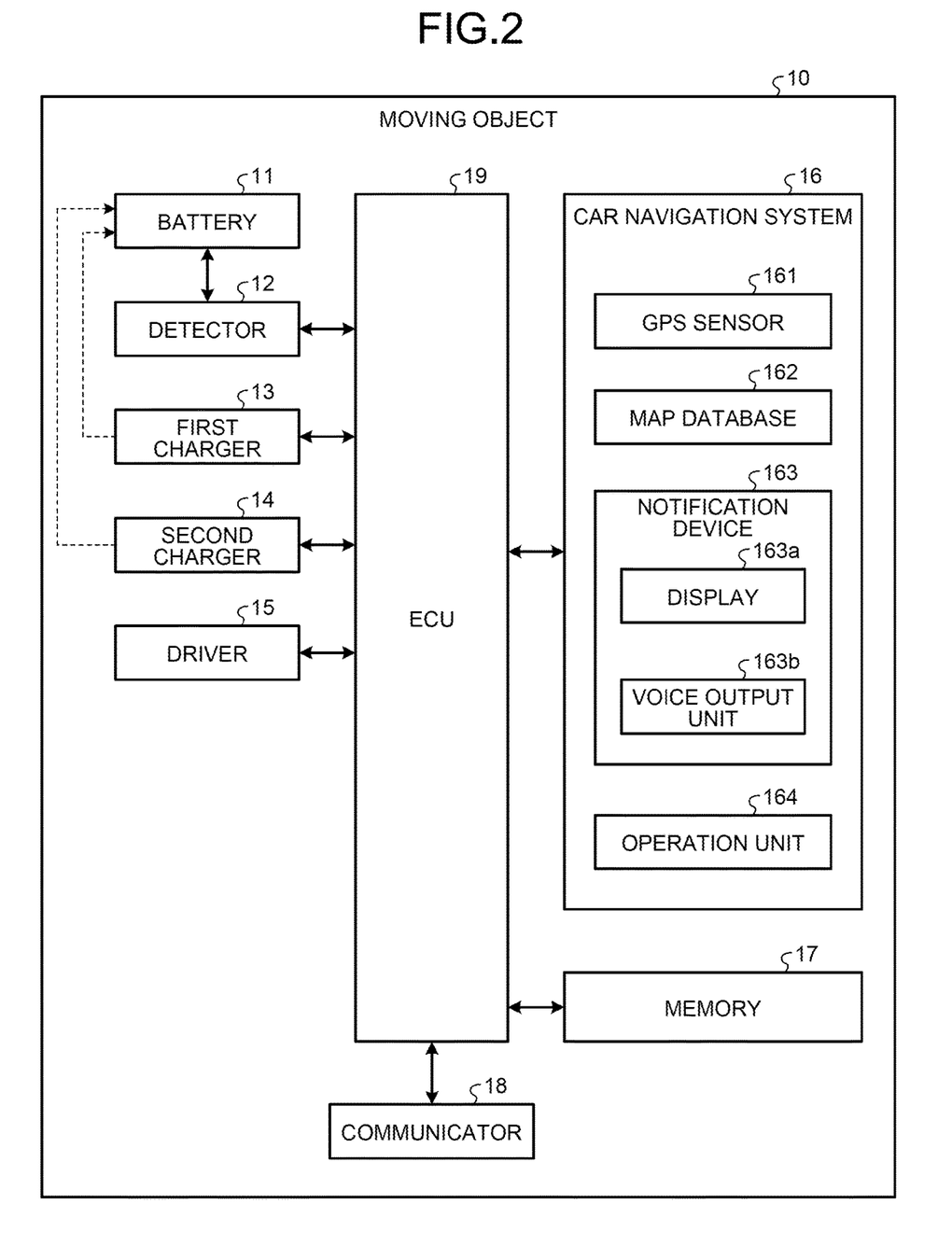
FIG. 2 is a block diagram illustrating the functional configuration of a moving object according to the embodiment.

First, the functional configurations of the moving objects $10_n$ to $10_{n+1}$ will be described. The moving objects $10_n$ to $10_{n+1}$ have a similar functional configuration. Therefore, in the following description, when any of the moving objects $10_n$ to $10_{n+1}$ is referred to, the moving object will be simply described as a moving object 10. FIG. 2 is a block diagram illustrating the functional configuration of the moving object 10.

The moving object 10 in FIG. 2 includes a battery 11, a detector 12, a first charger 13, a second charger 14, a driver 15, a car navigation system 16, a memory 17, a communicator 18, and an electronic control unit (ECU) 19. Furthermore, although an automobile such as a battery electric vehicle (BEV), a plug-in hybrid electric vehicle (PHEV), and a fuel cell electric vehicle (FCEV) will be described as the moving object 10 below, these are not limitations. For example, an electric bicycle such as a motorcycle, a bicycle, and a scooter including a motor and a battery, a tricycle, a bus, a truck, a ship, and a drone may also be applied. Moreover, the moving object 10 automatically moves toward a destination under the control of the server 40. Of course, the moving object 10 may move toward the destination desired by a user who uses (boards) the moving object 10 by the user operating a steering and the like.

The battery 11 includes a rechargeable secondary battery such as a nickel-hydrogen battery and a lithium-ion battery. The battery 11 stores high-voltage direct-current power for driving the moving object 10.

The detector 12 detects each of the state of charge (SOC), the temperature, the state of health (SOH), the voltage value, and the current value of the battery 11, and outputs the detection result to the ECU 19. The detector 12 includes various battery sensors, temperature sensors, and the like.

The first charger 13 is electrically connected to the battery 11, and may be electrically connected to a later-described charging device 30 via a charging port. The first charger 13 converts (transforms) alternating current supplied from the charging device 30 (power supply in usual mode using AC charging) into voltage and power that may be charged to the battery 11, and outputs the converted voltage and power. The first charger 13 includes an AC/DC converter, a DC/DC converter, and the like.

The second charger 14 is electrically connected to the battery 11, and may be electrically connected to the charging device 30 via a charging port. The second charger 14 converts (transforms) direct current supplied from the charging device 30 (power supply in rapid charging mode using DC charging) into voltage and power that may be charged to the battery 11, and outputs the converted voltage and power. The first charger 13 includes a DC/DC converter, a rectifier circuit, and the like.

The driver 15 supplies driving force to a driving wheel of the moving object 10 based on the power supplied from the battery 11 under the control of the ECU 19. The driver 15 includes a motor and the like.

The car navigation system 16 includes a global positioning system (GPS) sensor 161, a map database 162, a notification device 163, and an operation unit 164.

The GPS sensor 161 receives a signal from a plurality of GPS satellites or transmission antennas, and calculates the position (longitude and latitude) of the moving object 10 based on the received signal. The GPS sensor 161 includes a GPS reception sensor and the like. Note that, in the embodiment, the orientation accuracy of the moving object 10 may be improved by mounting a plurality of GPS sensors 161.

The map database 162 stores various pieces of map data. The map database 162 includes a recording medium such as a hard disk drive (HDD) and a solid state drive (SSD).

The notification device 163 includes a display 163a and a voice output unit 163b. The display 163a displays an image, a map, a video, and character information. The voice output unit 163b generates sound such as voice and warning sound. The display 163a includes a display device using a liquid crystal, organic electro luminescence (EL), and the like. The voice output unit 163b includes a speaker and the like.

The operation unit 164 receives inputs of user operations, and outputs signals in accordance with the received various operation contents to the ECU 19. The operation unit 164 includes a touch panel, a button, a switch, a jog dial, and the like.

The car navigation system 16 configured as described above superimposes the current position of the moving object 10 acquired by the GPS sensor 161 on a map corresponding to map data stored in the map database 162, thereby notifying the user of information including a road on which the moving object 10 is currently traveling, a route to a destination, and the like with the display 163a and the voice output unit 163b.

The memory 17 stores various pieces of information on the moving object 10. The memory 17 stores CAN data on the moving object 10 input from the ECU 19, various programs executed by the ECU 19, and the like. The memory 17 includes a dynamic random access memory (DRAM), a read only memory (ROM), a flash memory, a hard disk drive (HDD), a solid state drive (SSD), and the like.

The communicator 18 transmits CAN data and the like to the server 40 over the network NW under the control of the ECU 19. Here, the CAN data includes the state of charge (SOC), the SOH, and the like of the battery 11. The communicator 18 includes a communication module or the like capable of transmitting/receiving various pieces of information.

The ECU 19 includes a memory and a processor having hardware such as a central processing unit (CPU). The ECU 19 controls each unit of the moving object 10. The ECU 19 moves the moving object 10 to the charging device 30 or a predetermined place by controlling the driver 15 based on a signal and an instruction transmitted from the server 40 via the communicator 18, the position of the moving object 10 detected by the car navigation system 16, and the like.

Figure 3:
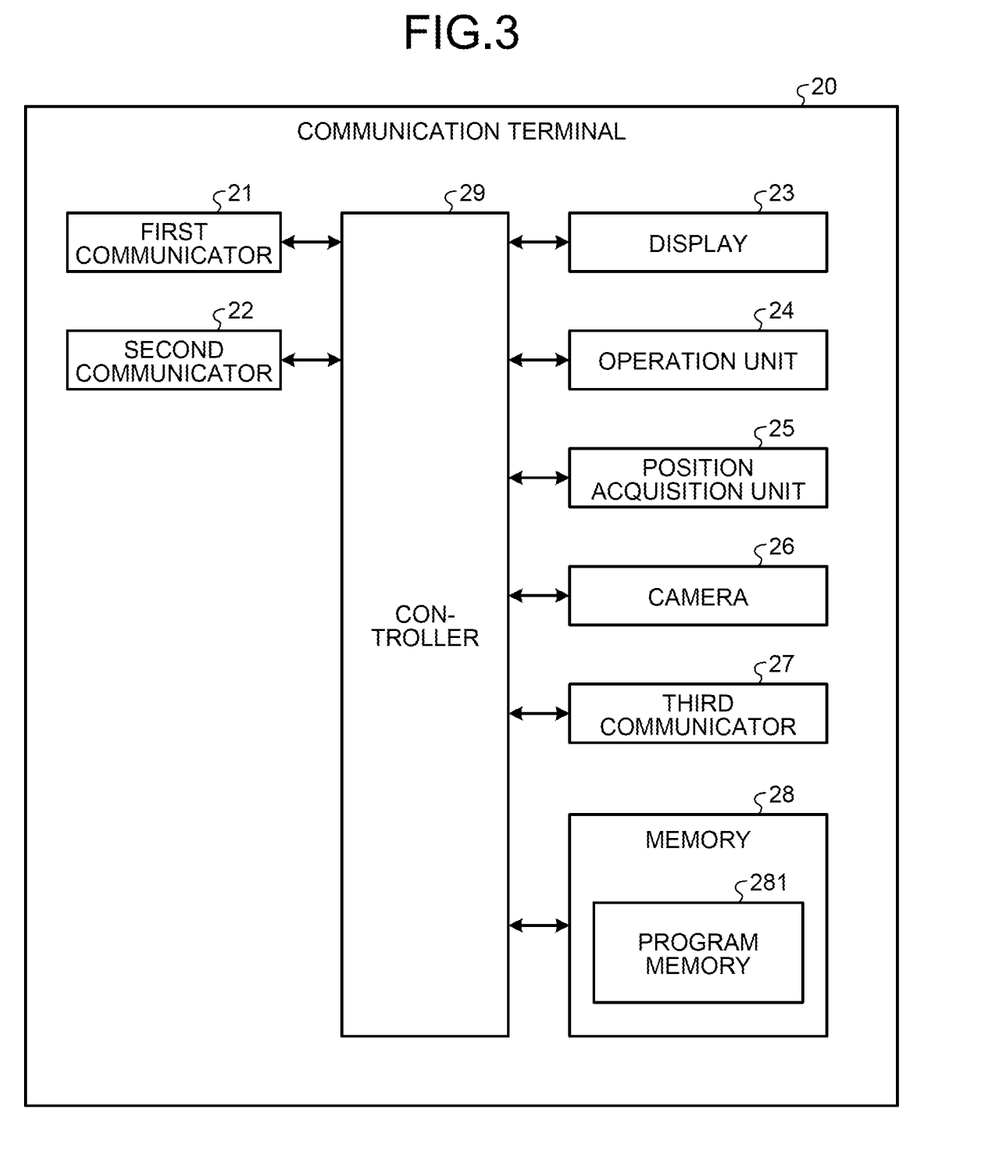
FIG. 3 is a block diagram illustrating the functional configuration of a communication terminal according to the embodiment.

Next, the functional configurations of the communication terminals $20_n$ to $20_{n+1}$ will be described. The communication terminals $20_n$ to $20_{n+1}$ have a similar functional configuration. Therefore, when any of the communication terminals $20_n$ to $20_{n+1}$ is referred to, the communication terminal will be simply described below as a communication terminal 20. FIG. 3 is a block diagram illustrating the functional configuration of the communication terminal 20.

The communication terminal 20 in FIG. 3 includes a first communicator 21, a second communicator 22, a display 23, an operation unit 24, a position acquisition unit 25, a camera 26, a third communicator 27, a memory 28, and a controller 29. Note that, although the communication terminal 20 will be described below as a mobile phone, the communication terminal 20 is not limited to the mobile phone. For example, a tablet terminal, a wearable device, and the like may be applied.

The first communicator 21 receives various pieces of information from the moving object 10 under the control of the controller 29, and outputs the received various pieces of information to the controller 29. The first communicator 21 includes a communication module capable of performing, for example, Bluetooth (registered trademark) and the like. Furthermore, the first communicator 21 communicates with a wearable device worn by a user, and acquires biological information detected by the wearable device.

The second communicator 22 receives various pieces of information from the moving object 10 under the control of the controller 29, and outputs the received various pieces of information to the controller 29. The second communicator 22 includes a communication module capable of performing Wi-Fi (registered trademark) and the like.

The display 23 displays various pieces of information under the control of the controller 29. The display 23 includes a display panel using a liquid crystal, organic electro luminescence (EL), and the like.

The operation unit 24 receives inputs of various user operations, and outputs signals corresponding to the received various operations to the controller 29. The operation unit 24 includes a touch panel, a switch, a button, and the like.

The position acquisition unit 25 acquires the position of the communication terminal 20, and outputs the acquired position to the controller 29. The position acquisition unit 25 is implemented by using a plurality of GPS reception sensors and the like.

The camera 26 generates image data by imaging a subject under the control of the controller 29, and outputs the image data to the controller 29. The camera 26 is implemented by using one or a plurality of optical systems and an image sensor of a charge coupled device (CCD) or a complementary metal oxide semiconductor (CMOS), which generate image data by capturing a subject image formed by the optical systems.

The third communicator 27 communicates with the server 40 via the network NW under the control of the controller 29, and transmits destination information on a destination set by a user via the operation unit 24. The third communicator 27 includes a communication module capable of performing a communication standard based on a mobile phone line, for example, a fourth-generation mobile communication system (4G), a fifth-generation mobile communication system (5G), and the like.

The memory 28 stores various pieces of information on the communication terminal 20 and various programs executed by the communication terminal 20. The memory 28 is implemented by using a DRAM, a ROM, a flash memory, an SSD, a memory card, and the like.

The controller 29 includes a memory and a processor having hardware such as a CPU. The controller 29 controls each unit of the communication terminal 20. Note that, in the embodiment, the controller 29 functions as a first processor.

Figure 4:
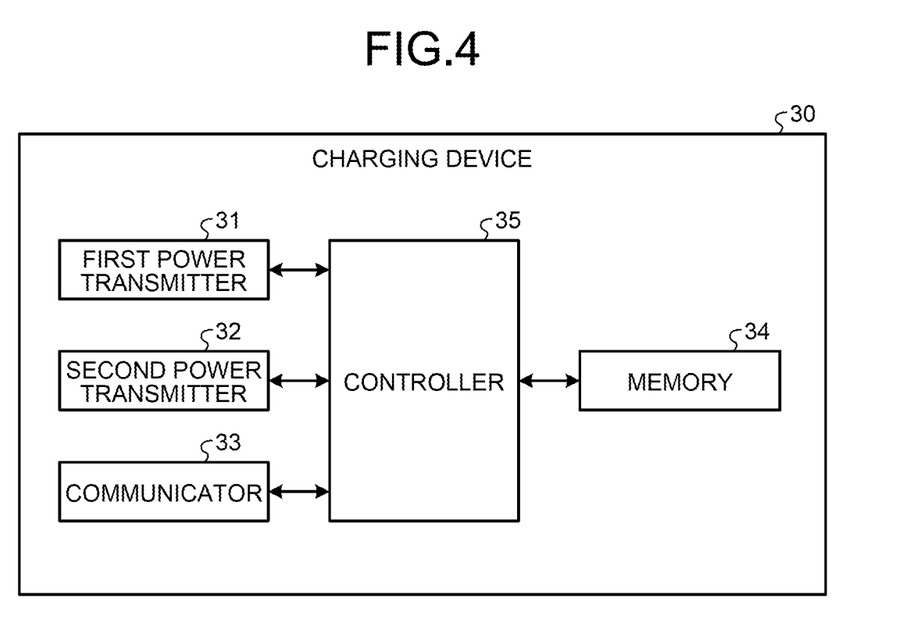
FIG. 4 is a block diagram illustrating the functional configuration of a charging device according to the embodiment.

Next, the functional configurations of the charging devices $30_n$ to $30_{n+1}$ will be described. The charging devices $30_n$ to $30_{n+1}$ have a similar functional configuration. Therefore, when any of the charging devices $30_n$ to $30_{n+1}$ is referred to, the charging device will be simply described below as the charging device 30. FIG. 4 is a block diagram illustrating the functional configuration of the charging device 30. Furthermore, at least one or more charging devices 30 are installed in charging facilities.

The charging device 30 in FIG. 4 includes a first power transmitter 31, a second power transmitter 32, a communicator 33, a memory 34, and a controller 35.

The first charger 13 of the moving object 10 is connected to the first power transmitter 31. The first power transmitter 31 converts alternating current of a predetermined voltage value (e.g., 6600 V) supplied from an external alternating current power source into direct current of a predetermined value (e.g., 200 V), and thereby supplies the converted current to the first charger 13 (usual charging). The first power transmitter 31 includes a connector connectable to the first charger 13 of the moving object 10, a cable that transfers power to the connector, an AC/DC converter, an inverter, a rectifier circuit, a transformer, a circuit breaker, and the like. Note that the first power transmitter 31 may supply power in a non-contact manner (wireless AC charging). In the case, either of a magnetic field coupling method or an electric field coupling method may be adopted as a power supply method.

The second power transmitter 32 converts alternating current of a predetermined voltage value (e.g., 6600 V) supplied from an external alternating current power source into direct current of a predetermined voltage value (e.g., 500 V), and thereby supplies the converted current to the second charger (rapid charging). The second power transmitter 32 includes a connector connectable to the second charger 14 of the moving object 10, a cable that transfers power to the connector, an AC/DC converter, an inverter, a rectifier circuit, a transformer, a circuit breaker, and the like.

The communicator 33 communicates with the moving object 10, the communication terminal 20, and the server 40 over the network NW, and transmits/receives various pieces of information under the control of the controller 35. The communicator 33 includes a communication module and the like.

The memory 34 stores various pieces of information on the charging device 30. The memory 34 includes a DRAM, a ROM, a flash memory, an SSD, and the like.

The controller 35 includes a memory and a processor having hardware such as a CPU. The controller 35 controls each unit of the charging device 30.

Figure 5:
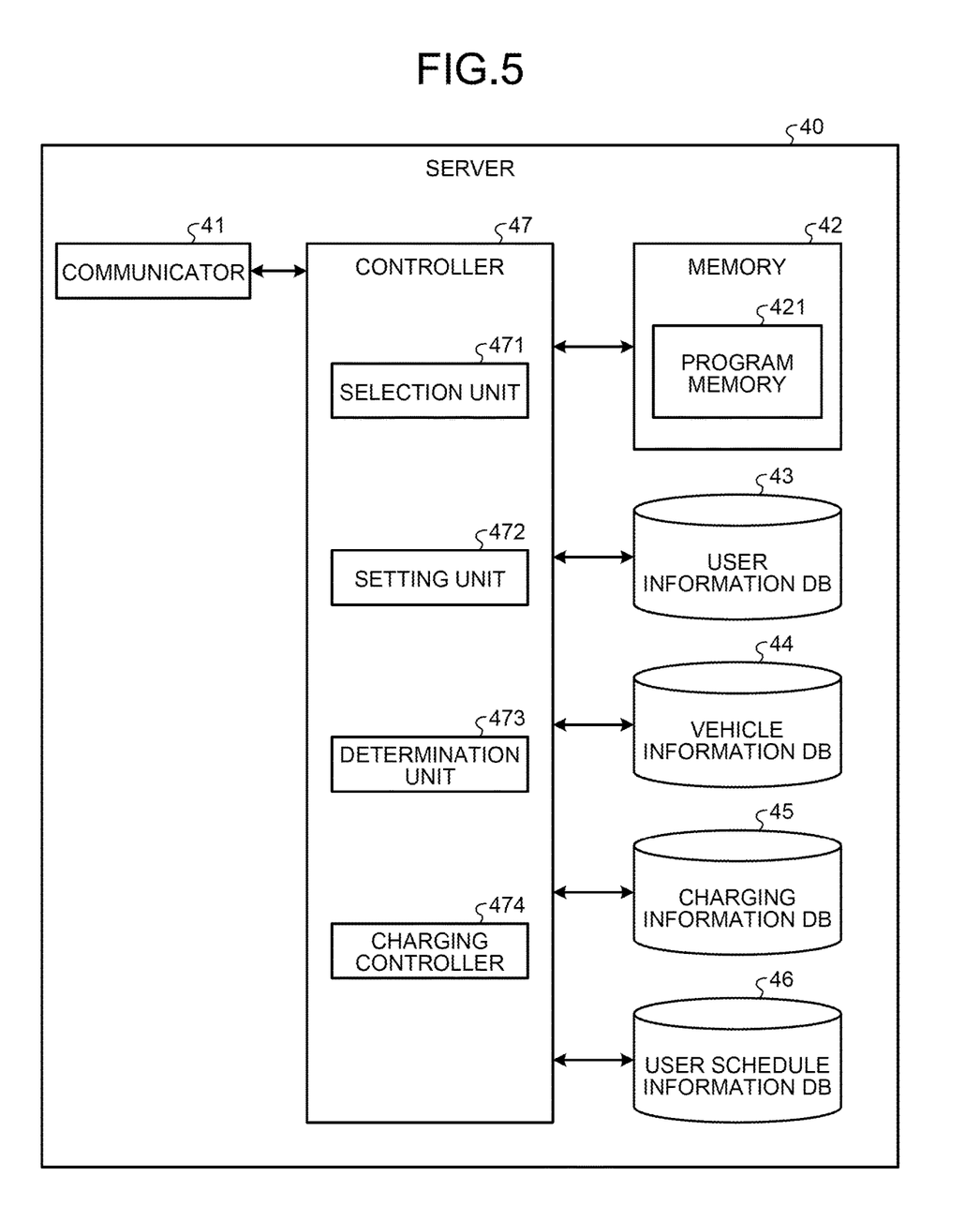
FIG. 5 is a block diagram illustrating the functional configuration of a server according to the embodiment.
Figure 6:
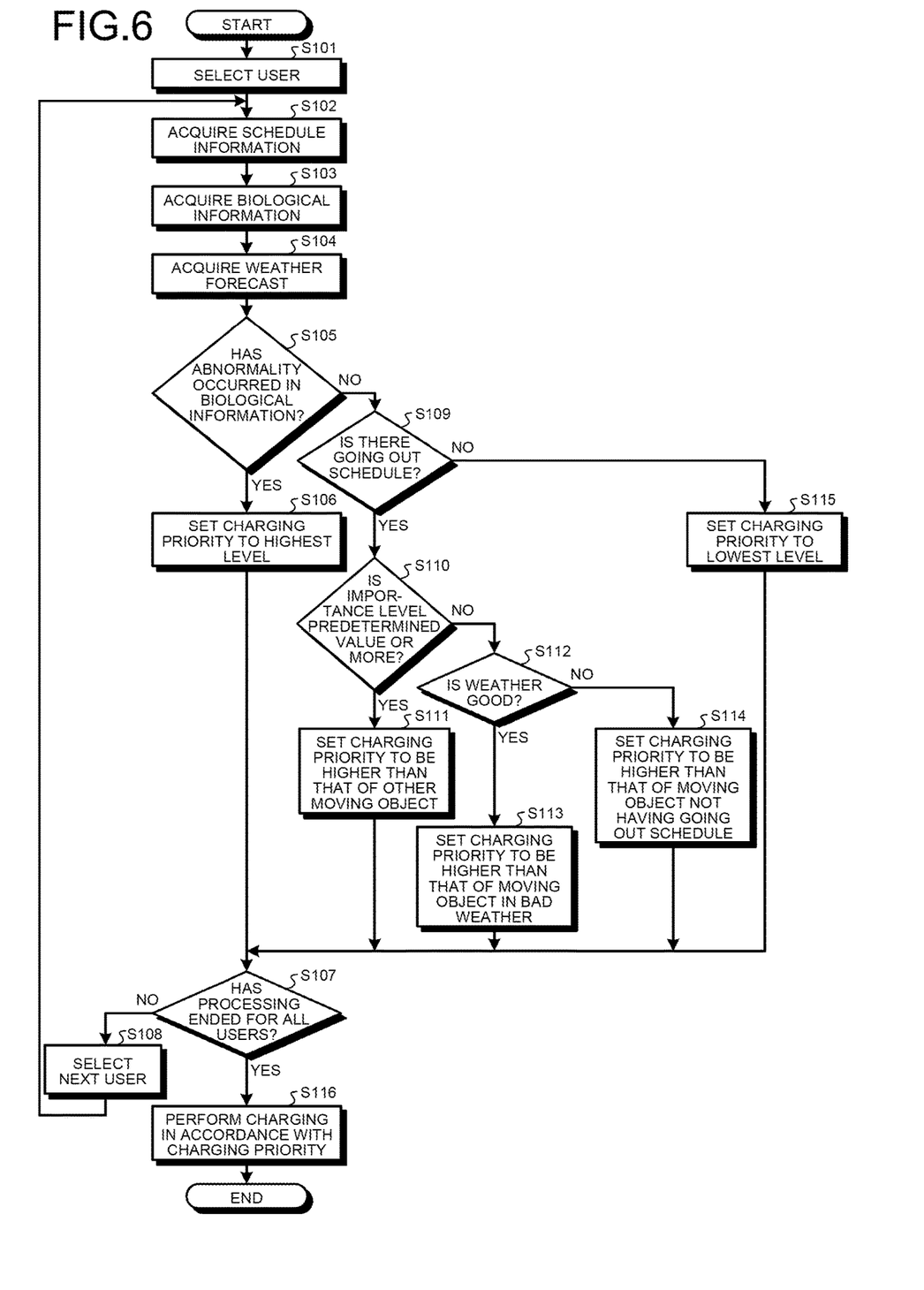
FIG. 6 is a flowchart outlining processing executed by the server according to the embodiment.

Next, the functional configuration of the server 40 will be described. FIG. 5 is a block diagram illustrating the functional configuration of the server 40.

The server 40 in FIG. 5 includes a communicator 41, a memory 42, a user information database 43 (hereinafter, referred to as "user information DB 43"), a vehicle information database 44 (hereinafter, referred to as "vehicle information DB 44"), a charging information database 45 (hereinafter, referred to as "charging information DB 45"), a user schedule information database 46 (hereinafter, referred to as "user schedule information DB 46"), and a controller 47.

The communicator 41 communicates with the moving object 10, the communication terminal 20, and the charging device 30 via the network NW under the control of the controller 47. The communicator 41 includes a communication module and the like.

The memory 42 stores various pieces of information on the server 40. Furthermore, the memory 42 includes a program memory 421 that stores various programs executed by the server 40. The memory 42 is implemented by using a DRAM, a ROM, a flash memory, an SSD, an HDD, a memory card, and the like.

The user information DB 43 stores user information. In the user information, terminal information for identifying the communication terminal 20 held by the user and user identification information for identifying the user are associated with each other. Here, the terminal information includes a device address, a telephone number, an e-mail address, and the like. Furthermore, the user identification information includes a name, an address, a birth date of a user, and an action history of the user based on information on the position of the communication terminal 20 of the user, and the like. The user information DB 43 includes an HDD, an SSD, and the like.

The vehicle information DB 44 stores vehicle information. In the vehicle information, vehicle identification information for identifying the moving object 10, information on the current state of the moving object 10, information on the current position of the moving object 10, and a plurality of moving objects 10 preliminarily associated with user identification information on a plurality of users are associated with each other. The vehicle identification information includes the vehicle type name, the model year, the owner, and the like of the moving object 10. Furthermore, the state information includes the state of charge of the battery 11 of the moving object 10, CAN data, and the like. The vehicle information DB 44 includes an HDD, an SSD, and the like.

The charging information DB 45 stores charging information. In the charging information, charging identification information for identifying the charging device 30, charging status information indicating the current charging status of the charging device 30, and installation information indicating an installation place of the charging device 30 are associated with each other. The charging identification information includes a mode of charging (a charging mode such as a usual charging mode (single-phase AC 200 V or 100 V) or a rapid charging mode) the charging device 30, the shape of a charging connector, a device address, and the like. The charging status information includes whether or not the moving object 10 is currently charged by the charging device 30, the scheduled completion time of charging of the battery 11 of the moving object 10, the charging status of the battery 11 of the moving object 10, and the like. The charging information DB 45 includes an HDD, an SSD, and the like.

The user schedule information DB 46 stores user schedule information. In the user schedule information, terminal information for identifying the communication terminal 20 held by a user, user identification information for identifying the user, and a schedule of the user input by the user are associated with each other. Here, the schedule of the user includes a position where the moving object 10 is scheduled to be used, a destination of the user, a scheduled use time of the user (scheduled going out time), a date and time when the user uses the moving object 10, vehicle identification information on the moving object 10 used by the user, presence or absence of a going out schedule of the user, the importance level of the going out schedule, and the like. Here, the importance level is obtained by quantifying the content performed at the place where the user goes or the content performed based on a reason for going out. For example, when the user goes out to a hospital, a higher numerical value is set as the importance level than that in the case where the user goes out to a retail store and the like. Moreover, when the user goes out for picking up or dropping off his/her child or family, a higher numerical value is set as the importance level than that in the case where the user goes out for shopping. Specifically, the importance level is set to "1" when the user goes out to a hospital, and is set to "0" when the user goes to a retail store. Moreover, the importance level is set to "1" when the user goes out for picking up or dropping off his/her child or family, and is set to "0" when the user goes out for shopping. The user schedule information DB 46 includes an HDD, an SSD, and the like.

The controller 47 includes a memory and a processor having hardware such as a CPU, a field-programmable gate array (FPGA), and a graphics processing unit (GPU). The controller 47 controls each unit of the server 40. The controller 47 includes a selection unit 471, a setting unit 472, a determination unit 473, and a charging controller 474.

In the selection unit 471, first, the selection unit 471 selects a first user from a plurality of users in a predetermined region. Specifically, the selection unit 471 sets a first user in charging priority allocation processing from a plurality of users in a predetermined region. In the charging priority allocation processing, charging priority is allocated to the moving object 10 preliminarily associated with a user. Here, the inside of a predetermined region is, for example, the inside of a region of 100 km×100 km. Of course, the predetermined region may be appropriately changed.

The setting unit 472 acquires schedule information on each of a plurality of users. Specifically, the setting unit 472 acquires the schedule information on each of a plurality of users from the user schedule information DB 46. Furthermore, the setting unit 472 sets a charging priority at the time of charging each of a plurality of moving objects 10 based on schedule information on each of the plurality of users. The plurality of moving objects 10 is preliminarily associated with each of the plurality of users, and has a rechargeable battery 11. Furthermore, the setting unit 472 acquires biological information on each of the plurality of users, and sets the charging priority of each of the plurality of moving objects 10 preliminarily associated with each of the plurality of users based on the biological information and the schedule information on each of the plurality of users. Specifically, the setting unit 472 acquires biological information detected by a wearable device worn by the user selected by the selection unit 471 via the communication terminal 20 of the user and the communicator 41 selected by the selection unit 471. Here, the biological information includes a body weight, a blood pressure, a pulse, a blood glucose level, a cholesterol level, a blood oxygen concentration, a body temperature, and the like. Furthermore, the setting unit 472 sets a charging priority of each of the plurality of moving objects 10 preliminarily associated with each of a plurality of users based on a determination result of the later-described determination unit 473. Furthermore, the setting unit 472 acquires a weather forecast in accordance with information on the position of a user from the weather server 50 via the communicator 41. Specifically, the setting unit 472 acquires information on the position of the communication terminal 20 of the user via the communicator 41, and acquires information on weather in a predetermined range (e.g., 100 km×100 km) based on the acquired position information from the weather server 50.

The determination unit 473 determines whether or not an abnormality has occurred in the biological information for each of the plurality of users acquired by the setting unit 472. Here, the case where the abnormality has occurred in the biological information means, for example, a maximum blood pressure of 40 mmHg or more, a blood glucose level of 200 mg/dL or more, a pulse of 100 beats/minute or more, a blood oxygen concentration of 90% or less, and a body temperature of 38 degrees or more. Of course, in addition to various numerical values, the determination unit 473 may determine whether or not the abnormality has occurred in user biological information by comparing user biological information accumulated for a predetermined period (e.g., one year) included in user information stored in the user information DB 43 with latest user biological information acquired by the setting unit 472. Furthermore, the determination unit 473 determines whether or not each of the plurality of users has a going out schedule based on schedule information on each of the plurality of users acquired by the setting unit 472. Moreover, the determination unit 473 determines whether or not the importance level of the going out schedule is a predetermined value or more for each of the plurality of users who has a going out schedule. Furthermore, the determination unit 473 determines whether or not the weather is good at a use time when the moving object 10 is to be used for each of the plurality of users based on a weather forecast acquired by the setting unit 472 from the weather server 50 and schedule information on each of the plurality of users.

The charging controller 474 sequentially charges each of the moving objects 10 in accordance with the charging priority set by the setting unit 472 for each of the plurality of moving objects 10 located in a predetermined region.

Next, processing executed by the server 40 will be described. FIG. 5 is a flowchart outlining processing executed by the server 40. Note that the server 40 performs the following processing at predetermined intervals, for example, daily intervals or every 12 hours for each predetermined region. Here, the inside of a predetermined region is, for example, the inside of a region of 100 km×100 km. Of course, the predetermined region may be appropriately changed.

As illustrated in FIG. 5, first, the selection unit 471 selects a first user from a plurality of users in a predetermined region (Step S101). Specifically, the selection unit 471 sets a first user in charging priority allocation processing based on user information stored in the user information DB 43 and vehicle information stored in the vehicle information DB 44. In the charging priority allocation processing, charging priority is allocated to the moving object 10 preliminarily associated with the first user among a plurality of users in a predetermined region.

Subsequently, the setting unit 472 acquires user schedule information selected by the selection unit 471 (Step S102). Specifically, the setting unit 472 acquires schedule information associated with the user (user identification information) selected by the selection unit 471 from the user schedule information DB 46.

Subsequently, the setting unit 472 acquires user biological information selected by the selection unit 471 via the communicator 41 (Step S103). Specifically, the setting unit 472 acquires biological information detected by a wearable device worn by the user selected by the selection unit 471 via the communication terminal 20 of the user and the communicator 41 selected by the selection unit 471. Note that, in addition to biological information detected by a wearable device worn by the user, the setting unit 472 may acquire biological information detected by various sensors installed in a house where the user lives or biological information detected by a monitoring camera and the like located in the vicinity of the user via the communicator 41.

Thereafter, the setting unit 472 acquires a weather forecast in accordance with information on the position of a user from the weather server 50 via the communicator 41 (Step S104). Specifically, the setting unit 472 acquires information on the position of the communication terminal 20 of the user via the communicator 41, and acquires information on weather in a predetermined range (e.g., 100 km×100 km) based on the acquired position information from the weather server 50.

The determination unit 473 determines whether or not an abnormality has occurred in the user biological information acquired by the setting unit 472 (Step S105). Specifically, when a difference between the user biological information in the user information stored in the user information DB 43 and the latest user biological information acquired by the setting unit 472 is a predetermined value or more, for example, 20% or more, the determination unit 473 may determine that an abnormality has occurred in the user biological information. When the determination unit 473 determines that an abnormality has occurred in the user biological information acquired by the setting unit 472 (Step S105: Yes), the server 40 proceeds to Step S106 described later. In contrast, when the determination unit 473 determines that an abnormality has not occurred in the user biological information acquired by the setting unit 472 (Step S105: No), the server 40 proceeds to Step S109 described later.

In Step S106, the setting unit 472 sets the charging priority to the highest such that the charging priority of the moving object 10 preliminarily associated with the user is higher than the charging priority of the moving object 10 preliminarily associated with another user. Specifically, the setting unit 472 sets the charging priority of the moving object 10 preliminarily associated with the user to "5", which is the highest in all stages. As a result, when the user feels that something is wrong with the user himself/herself, the user may quickly move to a hospital and the like since the moving object 10, which is preliminarily associated with the user himself/herself and scheduled to be used, has been already charged.

Subsequently, the determination unit 473 determines whether or not the charging priority allocation processing has ended for all users (Step S107). When the determination unit 473 determines that the charging priority allocation processing has ended for all users (Step S107: Yes), the server 40 proceeds to Step S116 described later. In contrast, when the determination unit 473 determines that the charging priority allocation processing has not ended for all users (Step S107: No), the server 40 proceeds to Step S108 described later.

In Step S108, the selection unit 471 selects the next user from a plurality of users in a predetermined region. After Step S108, the server 40 returns to Step S102.

In Step S109, the determination unit 473 determines whether or not the user has a going out schedule based on user schedule information acquired by the setting unit 472. When the determination unit 473 determines that the user has a going out schedule (Step S109: Yes), the server 40 proceeds to Step S110 described later. In contrast, when the determination unit 473 determines that the user does not have a going out schedule (Step S109: No), the server 40 proceeds to Step S115 described later.

In Step S110, the determination unit 473 determines whether or not the importance level of the going out schedule of the user is a predetermined value or more. When the determination unit 473 determines that the importance level of the going out schedule of the user is a predetermined value or more (Step S110: Yes), the server 40 proceeds to Step S111 described later. In contrast, when the determination unit 473 determines that the importance level of the going out schedule of the user is not a predetermined value or more (Step S110: No), the server 40 proceeds to Step S112 described later.

In Step S111, the setting unit 472 sets the charging priority of the moving object 10 preliminarily associated with a user having a going out schedule to be higher than the charging priority of the moving object 10 preliminarily associated with another user (user not having going out schedule). Specifically, the setting unit 472 sets the charging priority of the moving object 10 preliminarily associated with the user having a going out schedule to "4" in all stages. As a result, the user may visit a hospital or perform picking up or dropping off without delay since the moving object 10 to be used at the time of going out has been already charged. After Step S111, the server 40 proceeds to Step S107.

In Step S112, the determination unit 473 determines whether or not the weather is good during the time when the user having a going out schedule goes out based on a weather forecast acquired by the setting unit 472. When the determination unit 473 determines that the weather is good during the time when the user having a going out schedule goes out (Step S112: Yes), the server 40 proceeds to Step S113 described later. In contrast, when the determination unit 473 determines that the weather is not good during the time when the user having a going out schedule goes out (Step S112: No), the server 40 proceeds to Step S114 described later.

In Step S113, the setting unit 472 sets the charging priority of the moving object 10 preliminarily associated with the user having a going out schedule to be higher than the charging priority of the moving object 10 preliminarily associated with another user not having a going out schedule. The moving object 10 is preliminarily associated with another user not having a going out schedule. Specifically, the setting unit 472 sets the charging priority of the moving object 10 preliminarily associated with the user having a going out schedule to "3" in all stages. In the case, the user having a going out schedule is highly likely to use the moving object 10 during the going out time. Therefore, the server 40 may efficiently perform charging with each of the plurality of charging devices 30 in a predetermined region without waste by setting the charging priority of the moving object 10 preliminarily associated with the user having a going out schedule to be higher. After Step S113, the server 40 proceeds to Step S107 described later.

In Step S114, the setting unit 472 sets the charging priority of the moving object 10 preliminarily associated with a user having a going out schedule to be higher than the charging priority of the moving object 10 preliminarily associated with a user not having a going out schedule. Specifically, the setting unit 472 sets the charging priority of the moving object 10 preliminarily associated with the user having a going out schedule to "2" in all stages. In the case, even if the user is scheduled to go out, the user is not highly likely to user the moving object 10 due to bad weather. Therefore, the server 40 may efficiently perform charging with each of the plurality of charging devices 30 in a predetermined region without waste by setting the charging priority of the moving object 10 preliminarily associated with the user not having a going out schedule to be higher. After Step S114, the server 40 proceeds to Step S107 described later.

In Step S115, the setting unit 472 sets the charging priority of the moving object 10 preliminarily associated with the user not having a going out schedule to be the lowest. Specifically, the setting unit 472 sets the charging priority of the moving object 10 preliminarily associated with the user not having a going out schedule to "1" in all stages. As a result, the server 40 may efficiently perform charging without waste with each of the plurality of charging devices 30 in a predetermined region by prioritizing the charging of another moving object 10 since the user not having a going out schedule is not highly likely to use the moving object 10. After Step S115, the server 40 proceeds to Step S107 described later.

In Step S116, the charging controller 474 sequentially charges each of the moving objects 10 in accordance with the charging priority set by the setting unit 472 for each of the plurality of moving objects 10 located in a predetermined region. As a result, the server 40 may efficiently perform charging without waste with each of the plurality of charging devices 30 in the predetermined region. After Step S116, the server 40 ends the processing.

According to the embodiment, the setting unit 472 acquires schedule information on each of a plurality of users, and sets a charging priority at the time of charging each of a plurality of moving objects 10 based on schedule information on each of the plurality of users. The plurality of moving objects 10 is preliminarily associated with each of the plurality of users, and has a rechargeable battery 11. Then, the charging controller 474 charges each of the plurality of moving objects 10 based on the charging priority set by the setting unit 472 for the plurality of moving objects 10 preliminarily associated with each of the plurality of users. As a result, the moving object 10 may be charged in consideration of the use timing of the user.

Furthermore, according to the embodiment, the setting unit 472 acquires biological information on each of the plurality of users, and sets the charging priority at the time of charging each of the plurality of moving objects 10 based on the biological information and the schedule information on each of the plurality of users. Therefore, even when only the limited number of charging devices 30 are installed in the predetermined region, each of the plurality of moving objects 10 may be efficiently charged by the plurality of charging devices 30.

Furthermore, according to the embodiment, the determination unit 473 determines whether or not an abnormality has occurred in the biological information for each of the plurality of users. Then, the setting unit 472 sets the charging priority of the moving object 10 preliminarily associated with a user, who is determined to have an abnormality in the biological information by the determination unit 473, to be higher than that of the moving object 10 preliminarily associated with another user. Therefore, when the user who has abnormality in the biological information uses the moving object 10, the user may immediately use the moving object 10 since the charging of the battery 11 of the moving object 10 has been ended.

Furthermore, according to the embodiment, the determination unit 473 determines whether or not each of the plurality of users has a going out schedule based on the schedule information. Then, the setting unit 472 sets the charging priority of the moving object 10 preliminarily associated with a user, who is determined to have a going out schedule by the determination unit 473, to be higher than that of the moving object 10 preliminarily associated with a user determined not to have a going out schedule. As a result, the server 40 may efficiently perform charging without waste with each of the plurality of charging devices 30 in a predetermined region by prioritizing the charging of the other moving object 10 since the user not having a going out schedule is not highly likely to use the moving object 10 preliminarily associated with the user not having a going out schedule.

Furthermore, according to the embodiment, the determination unit 473 determines whether or not the importance level is a predetermined value or more for each of the plurality of users having a going out schedule. Then, the setting unit 472 sets the charging priority of the moving object 10 preliminarily associated with a user having an importance level of a predetermined value or more by the determination unit 473 to be higher than that of the moving object 10 preliminarily associated with a user not having an importance level of a predetermined value or more. As a result, the user may visit a hospital or perform picking up or dropping off since the moving object 10 to be used at the time of going out has been already charged.

Furthermore, according to the embodiment, the determination unit 473 determines whether or not the weather is good during the time when each of the plurality of users having a going out schedule goes out based on a weather forecast and schedule information acquired by the setting unit 472. Then, the setting unit 472 sets the charging priority of the moving object 10 preliminarily associated with a user, who is determined to have a good weather during a going out time, to be higher than that of the moving object 10 preliminarily associated with a user determined not to have a good weather during a going out time. As a result, the server 40 may efficiently perform charging without waste with each of the plurality of charging devices 30 in the predetermined region.

Furthermore, according to the embodiment, the setting unit 472 sets the charging priority of the moving object 10 preliminarily associated with a user, who is determined not to have a good weather during a going out time of the user, to be higher than that of the moving object 10 preliminarily associated with a user not having a going out schedule. Therefore, the server 40 may efficiently perform charging without waste with each of the plurality of charging devices 30 in the predetermined region.

Note that, although, in the embodiment, the setting unit 472 sets the charging priority of the moving object 10 preliminarily associated with a user, who is determined not to have a good weather during a going out time of the user, to be higher than that of the moving object 10 preliminarily associated with a user not having a going out schedule, power may be discharged from the battery 11 of the moving object 10 preliminarily associated with the user not having a going out schedule to the other moving object 10 without setting the charging priority. As a result, charging may be efficiently performed without waste with each of the plurality of charging devices 30 in a predetermined region.

Furthermore, in a charging system according to the embodiment, a "unit" may be replaced with a "circuit" or the like. For example, a controller may be replaced with a control circuit.

Furthermore, a program to be executed by a charging system according to the embodiment may be provided after being stored in a computer-readable recording medium such as a CD-ROM, a flexible disk (FD), a CD-R, a digital versatile disk (DVD), a USB medium, and a flash memory as file data in an installable format or an executable format.

Furthermore, the program to be executed by the charging system according to the embodiment may be provided by being stored in a computer connected to a network such as the Internet and downloaded via the network.

Note that, although, in the description of the flowcharts in the present specification, the context of processing between steps is clearly indicated by using expressions such as "first", "thereafter", and "subsequently", the order of processing necessary for implementing the embodiment is not uniquely determined by these expressions. That is, the order of processing in the flowcharts described in the specification may be changed within a consistent range.

According to the present disclosure, an effect of allowing a moving object to be charged in consideration of the timing when a user uses the moving object is exhibited.

Although the disclosure has been described with respect to the specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A server comprising
a processor configured to:
   acquire schedule information on each of a plurality of users;
   set a charging priority at a time of charging each of a plurality of moving objects based on the schedule information on each of the plurality of users, each of the plurality of moving objects being preliminarily associated with each of the plurality of users, and including a rechargeable secondary battery;
   charge each of the plurality of moving objects based on the charging priority;
   acquire biological information on each of the plurality of users;
   set the charging priority of each of the plurality of moving objects based on the biological information and the schedule information;
   determine whether or not an abnormality has occurred in the biological information for each of the plurality of users; and
   set the charging priority of the moving object preliminarily associated with the user determined to have the abnormality in the biological information to be higher than that of the moving object preliminarily associated with another user.

2. The server according to claim 1, wherein
the schedule information includes presence or absence of a going out schedule of the user, and
the processor is configured to:
   determine whether or not each of the plurality of users has the going out schedule based on the schedule information; and
   set the charging priority of the moving object preliminarily associated with the user having the going out schedule to be higher than that of the moving object preliminarily associated with the user not having the going out schedule.

3. The server according to claim 2, wherein
the schedule information includes an importance level of the going out schedule, and
the processor is configured to:
   determine whether or not the importance level is a predetermined value or more for each of the plurality of users having the going out schedule; and
   set the charging priority of the moving object preliminarily associated with the user having the importance level of the predetermined value or more to be higher than that of the moving object preliminarily associated with the user having the importance level under the predetermined value.

4. The server according to claim 3, wherein the processor is configured to:
   acquire a weather forecast;
   determine whether or not weather is good during a going out time of the user having the going out schedule based on the weather forecast; and
   set the charging priority of the moving object preliminarily associated with the user determined to have good weather during the going out time to be higher than that of the moving object preliminarily associated with the user determined not to have good weather during the going out time.

5. The server according to claim 4, wherein the processor is configured to set the charging priority of the moving object preliminarily associated with the user determined not to have good weather during the going out time to be higher than that of the moving object preliminarily associated with the user not having the going out schedule.

6. A charging system comprising:
a plurality of moving objects each including a rechargeable secondary battery; and
a server including a processor configured to:
   acquire schedule information on each of the plurality of users;
   set a charging priority at a time of charging each of the plurality of moving objects preliminarily associated with each of the plurality of users based on the schedule information on each of the plurality of users;
   charge each of the plurality of moving objects based on the charging priority;
   acquire biological information on each of the plurality of users;
   set the charging priority of each of the plurality of moving objects based on the biological information and the schedule information
   determine whether or not an abnormality has occurred in the biological information for each of the plurality of users; and
   set the charging priority of the moving object preliminarily associated with the user determined to have the abnormality in the biological information to be higher than that of the moving object preliminarily associated with another user.

7. The charging system according to claim 6, wherein
the schedule information includes presence or absence of the going out schedule of the user, and
the processor is configured to:
   determine whether or not each of the plurality of users has the going out schedule based on the schedule information; and
   set the charging priority of the moving object preliminarily associated with the user having the going out schedule to be higher than that of the moving object preliminarily associated with the user not having the going out schedule.

8. The charging system according to claim 7, wherein
the schedule information includes an importance level of the going out schedule, and
the processor is configured to:
   determine whether or not the importance level is a predetermined value or more for each of the plurality of users having the going out schedule; and set the charging priority of the moving object preliminarily associated with the user having the importance level of the predetermined value or more to be higher than that of the moving object preliminarily associated with the user having the importance level under the predetermined value.

9. The charging system according to claim 8, wherein the processor is configured to:
acquire a weather forecast;
determine whether or not weather is good during a going out time of the user having the going out schedule based on the weather forecast; and
set the charging priority of the moving object preliminarily associated with the user determined to have good weather during the going out time to be higher than that of the moving object preliminarily associated with the user determined not to have good weather during the going out time.

10. The charging system according to claim 9, wherein the processor is configured to set the charging priority of the moving object preliminarily associated with the user determined not to have good weather during the going out time to be higher than that of the moving object preliminarily associated with the user not having a going out schedule.

11. A non-transitory computer-readable recording medium on which an executable program is recorded, the program causing a processor of a computer to execute:
acquiring schedule information on each of a plurality of users;
setting a charging priority at a time of charging each of a plurality of moving objects based on the schedule information on each of the plurality of users, each of the plurality of moving objects being preliminarily associated with each of the plurality of users, and including a rechargeable secondary battery;
charging each of the plurality of moving objects based on the charging priority;
acquiring biological information on each of the plurality of users;
setting the charging priority of each of the plurality of moving objects based on the biological information and the schedule information;
determining whether or not an abnormality has occurred in the biological information for each of the plurality of users; and
setting the charging priority of the moving object preliminarily associated with the user determined to have the abnormality in the biological information to be higher than that of the moving object preliminarily associated with another user.

12. The non-transitory computer-readable recording medium according to claim 11, wherein
the schedule information includes presence or absence of a going out schedule of the user, and
the program causes the processor to execute:
determining whether or not each of the plurality of users has the going out schedule based on the schedule information; and
setting the charging priority of the moving object preliminarily associated with the user having the going out schedule to be higher than that of the moving object preliminarily associated with the user not having the going out schedule.

13. The non-transitory computer-readable recording medium according to claim 12, wherein
the schedule information includes an importance level of the going out schedule, and
the program causes the processor to execute:
determining whether or not the importance level is a predetermined value or more for each of the plurality of users having the going out schedule; and
setting the charging priority of the moving object preliminarily associated with the user having the importance level of the predetermined value or more to be higher than that of the moving object preliminarily associated with the user having the importance level under the predetermined value or more.

14. The non-transitory computer-readable recording medium according to claim 13, wherein the program causes the processor to execute:
acquiring a weather forecast;
determining whether or not weather is good during a going out time of the user having the going out schedule based on the weather forecast; and
setting the charging priority of the moving object preliminarily associated with the user determined to have good weather during the going out time to be higher than that of the moving object preliminarily associated with the user determined not to have good weather during the going out time.

* * * * *